United States Patent
Tu et al.

(10) Patent No.: US 11,445,923 B2
(45) Date of Patent: Sep. 20, 2022

(54) METHOD AND DEVICE FOR ESTABLISHING BLOOD VESSEL CROSS-SECTION FUNCTION, BLOOD STRESS VESSEL PRESSURE DIFFERENCE AND BLOOD VESSEL STRESS

(71) Applicant: Shanghai Pulse Medical Technology, Inc., Shanghai (CN)

(72) Inventors: Shengxian Tu, Shanghai (CN); Jiayue Huang, Shanghai (CN); Jingfeng Han, Shanghai (CN)

(73) Assignee: Shanghai Pulse Medical Technology, Inc., Shanghai (CN)

( * ) Notice: Subject to any disclaimer, the term of this patent is extended or adjusted under 35 U.S.C. 154(b) by 0 days.

(21) Appl. No.: 17/283,226

(22) PCT Filed: Feb. 28, 2019

(86) PCT No.: PCT/CN2019/076511
§ 371 (c)(1),
(2) Date: Apr. 6, 2021

(87) PCT Pub. No.: WO2020/107732
PCT Pub. Date: Jun. 4, 2020

(65) Prior Publication Data
US 2021/0345889 A1   Nov. 11, 2021

(30) Foreign Application Priority Data
Nov. 30, 2018   (CN) .......................... 201811454057.3

(51) Int. Cl.
*A61B 5/021* (2006.01)
*A61B 5/00* (2006.01)

(52) U.S. Cl.
CPC ............ *A61B 5/021* (2013.01); *A61B 5/4887* (2013.01)

(58) Field of Classification Search
CPC .............................. A61B 5/021; A61B 5/4887
See application file for complete search history.

(56) References Cited

U.S. PATENT DOCUMENTS

| 2015/0245776 A1 | 9/2015 | Hirohata et al. |
| 2015/0268039 A1* | 9/2015 | Tu .......................... A61B 6/481 702/19 |

(Continued)

FOREIGN PATENT DOCUMENTS

| CN | 103077550 A | 5/2013 |
| CN | 103190932 A | 7/2013 |

(Continued)

OTHER PUBLICATIONS

Steele et al. 2003 IEEE Trans. Biomed. Engin. 50:649-656 (Year: 2003).*

(Continued)

*Primary Examiner* — Colin T. Sakamoto
*Assistant Examiner* — Patrick M Mehl
(74) *Attorney, Agent, or Firm* — Maschoff Brennan

(57) ABSTRACT

A blood vessel cross-section function, a blood vessel pressure difference, and blood vessel stress may be established. A method for establishing a blood vessel cross-section function may include: obtaining image data in at least one cardiac cycle; selecting multiple feature times during the one cardiac cycle; generating spatial models of a target region blood vessel corresponding to each of the feature times according to the image data; establishing a first cross-section model of the target region blood vessel at each position along an axial direction of the target region blood vessel according to each of the spatial models; and establishing a corresponding first cross-section function according to each first cross-section model. Actual conditions of blood vessels may be reflected more accurately, and may provide an intermediate variable with less error for subsequent analysis (Continued)

operations, so that the later calculated value is closer to the actual value.

10 Claims, 6 Drawing Sheets

(56) References Cited

U.S. PATENT DOCUMENTS

| | | |
|---|---|---|
| 2017/0071486 A1 | 3/2017 | Belleville et al. |
| 2018/0071027 A1 | 3/2018 | Taylor |
| 2018/0344173 A1 | 12/2018 | Tu et al. |

FOREIGN PATENT DOCUMENTS

| | | | |
|---|---|---|---|
| CN | 103300820 A | 9/2013 | |
| CN | 105326486 A | 2/2016 | |
| CN | 105559810 A | 5/2016 | |
| CN | 107123159 A | 9/2017 | |
| CN | 107665737 A | 2/2018 | |
| CN | 106570313 A | 3/2018 | |
| CN | 108717874 A | 10/2018 | |
| CN | 108742587 A | 11/2018 | |
| CN | 108784676 A | 11/2018 | |
| JP | 2018503419 A | 2/2018 | |
| JP | 2018102589 A * | 7/2018 | ............... A61B 8/04 |
| WO | 0113779 A2 | 3/2001 | |
| WO | 2017097074 | 6/2017 | |
| WO | WO2017097073 A1 * | 6/2017 | ............. A61B 5/021 |

OTHER PUBLICATIONS

State Intellectual Property Office; Search Report issued in No. 2018114540573.

State Intellectual Property Office; Search Report issued in No. 2018114540573 dated Oct. 29, 2019.

State Intellectual Property Office; Search Report issued in No. 2018114540573 dated Feb. 3, 2020.

State Intellectual Property Office; Decision for Rejection issued in No. 2018114540573 dated May 26, 2020.

State Intellectual Property Office; Decision of Re-Examination issued in No. 2018114540573 dated Oct. 15, 2020.

State Intellectual Property Office; Notice of Allowance issued in No. 2018114540573 dated Dec. 8, 2020.

* cited by examiner

METHOD AND DEVICE FOR ESTABLISHING BLOOD VESSEL CROSS-SECTION FUNCTION, BLOOD STRESS VESSEL PRESSURE DIFFERENCE AND BLOOD VESSEL STRESS

CROSS-REFERENCE TO RELATED APPLICATIONS

This application is a national phase application of International Patent Application No. PCT/CN2019/076511, filed on Feb. 28, 2019, which claims the benefit of CN 201811454057.3, filed Nov. 30, 2018, both of which are incorporated by reference herein in their entirety.

FIELD

The invention relates to the field of medical instruments, especially to method and device for establishing blood vessel cross-section function, blood vessel pressure difference and blood vessel stress.

BACKGROUND

The deposition of lipids and carbohydrates on the walls of blood vessels in human blood will form plaques on the walls of the blood vessels, which in turn will lead to stenosis of the blood vessels. In particular, stenosis of blood vessels near the coronary artery of the heart will lead to insufficient blood supply to the heart muscle, and induce coronary heart disease, angina pectoris and other diseases, posing a serious threat to human health.

In many coronary artery physiology assessment techniques, blood flow reserve fraction (FFR) is currently known as the most accurate functional assessment indicator.

The blood flow reserve fraction (FFR) is calculated from blood flow pressure Pa at the proximal end of the blood vessel in the target region and the difference $\Delta p$ between the blood flow pressure at the proximal end and distal end of the blood vessel in the target region.

However, the size of the plaque, the length of the plaque, the angle at which the plaque is formed, and the shape of the plaque and change of the plaque all affect the calculation of the difference $\Delta p$ in blood flow pressure. In the prior art, when the difference $\Delta p$ of the blood flow pressure is calculated, none of the above factors of the plaque is considered, so the calculation result has a large error with the actual value.

In order to solve the above problems, it has been proposed to obtain a cross cross-section at each position of a blood vessel in a target region to obtain a form of a lumen at different positions, and to consider factors such as the length of the plaque and the shape of the plaque.

However, for the blood vessels at the same location, the lumen form at different points in time is also different. Therefore, there is still a certain error in the calculation results.

SUMMARY

In order to solve the above problems, an objective of the present invention is to provide a method for establishing a blood vessel cross-section function with less error.

The present invention provides a method of establishing a blood vessel cross-section function, including the following steps:

obtaining image data in at least one cardiac cycle;
selecting a plurality of feature times during the one cardiac cycle;
generating spatial models of a target region blood vessel corresponding to each of the feature times according to the image data;
establishing a first cross-section model of the target region blood vessel at each position along an axial direction of the target region blood vessel according to each of the spatial models; and
establishing a corresponding first cross-section function according to each first cross-section model.

Further, the method includes:
along time series, the plurality of feature times are sequentially $t_1, t_2, \ldots, t_q$; along the axial direction of the target region blood vessel, the first cross-section functions corresponding to the first cross-section models at each position $1, 2, \ldots, r$ from a proximal end to a distal end of the target region blood vessel are $d_1, d_2, \ldots, d_r$, establishing a first cross-section matrix A according to a correspondence relationship between the first cross-section function, and the feature time and the position, $$A = \begin{bmatrix} A_{11} & A_{12} & \ldots & A_{1q} \\ A_{21} & A_{22} & \ldots & A_{2q} \\ \vdots & \vdots & \vdots & \vdots \\ A_{r1} & A_{r2} & \ldots & A_{rq} \end{bmatrix}$$

wherein, $A_{rq}$ is the first cross-section function $d_r$ corresponding to the first cross-section model at the feature time $t_q$, at the position r of the target region blood vessel; q=r or q≠r, and q and r are positive integers.

Further, the method including:
establishing a first difference function between the first cross-section functions corresponding to the two adjacent positions of the target region blood vessels at each feature time, along a column direction, according to the first cross-section matrix A.

Further, the method comprising:
according to the first difference function, establishing a first variation function f(x) of the target region blood vessel at each feature time that is changed with a distance x from a reference point to any position thereof.

Further, the first cross-section model includes a second cross-section model at different scales, and the method further including:
establishing a corresponding second cross-section function according to the second cross-section model at each scale; and
according to the correspondence relationship between the second cross-section function and the feature time and position, establishing a second cross-section matrix at different scales,
wherein, the scale is the distance between two adjacent positions. Further, the scale includes a first scale, a second scale, . . . , an $n^{th}$ scale, and the method including:
establishing a second difference function between the second cross-section functions corresponding to two adjacent positions of the target region blood vessels at different scales, along the column direction, according to the second cross-section matrix at each scale; and
establishing a second variation function $f_1(x), f_2(x), \ldots, f_n(x)$ of the corresponding target region blood vessel that is changed with a distance x from its any position to the reference point, according to the second difference function at the first scale, the second scale, ..., the $n^{th}$ scale;

wherein n is a positive integer greater than 1.

Further, the method including:

establishing a first difference function between the first cross-section functions corresponding to the two adjacent feature times of the target region blood vessels at each position along a row direction according to the first cross-section matrix A.

Further, the first cross-section function includes one or more of the following: an area function, a diameter function, a perimeter function, and an edge distance function.

The present invention further provides a method for obtaining a blood vessel pressure difference, including:

the above method of establishing a blood vessel cross-section function;

obtaining a blood flow model of a target region blood vessel according to image data;

obtaining a blood flow velocity V of a target region blood vessel according to the blood flow model;

obtaining a first blood vessel pressure difference $\Delta p_1$ at each feature time according to a blood flow velocity V and a second variation function $f_1(x), f_2(x), \ldots, f_n(x)$; and weighting and summing the first blood vessel pressure difference $\Delta p_1$ according to a ratio of a time interval between each feature time and the adjacent feature time in one cardiac cycle, so as to obtain the second blood vessel pressure difference $\Delta p_2$.

Further, a calculation formula of the first blood vessel pressure difference $\Delta p_1$ at different scales is:

$$\Delta p_1 = (c_1 V + c_2 V^2 + \ldots + c_m V^m) * [\alpha_1 * \int\!\!\int f_1(x)dx + \alpha_2 * \int\!\!\int f_2(x)dx + \ldots + \alpha_n * \int\!\!\int f_n(x)dx], \text{ wherein,}$$

$c_1, c_2, \ldots, c_m$ are reference coefficients of blood flow velocity V, respectively;

$\alpha_1, \alpha_2, \ldots, \alpha_n$ are weighting coefficients of the second variation function $f_1(x), f_2(x), \ldots, f_n(x)$ at different scales, respectively;

m, n are positive integers.

Further, the method further including:

obtaining regional information of a coronary system where the lesion is located according to each spatial model; and correcting the first blood vessel pressure difference $\Delta p_1$ according to the regional information, so as to obtain a corrected third blood vessel pressure difference $\Delta p_3$, wherein, the third blood vessel pressure difference $\Delta p_3$ and the first blood vessel pressure difference $\Delta p_1$ satisfy the following relationship:

$$\Delta p_3 = \omega * \Delta p_1, \omega \text{ is a correction parameter, and } 0.5 \leq \omega \leq 1.$$

Further, the regional information includes one or more of the following: a left main artery, a left anterior descending artery, a left circumflex artery, a right coronary artery, and a branch vessel.

Further, the correction parameter w satisfies one or more of the following:

when the lesion is in the left main artery, the correction parameter $\omega=1$;

when the lesion is in the left anterior descending artery, the correction parameter $\omega=0.9\sim1.0$;

when the lesion is in the left circumflex artery, the correction parameter $\omega=0.65\sim0.85$;

when the lesion is in the right coronary artery, the correction parameter $\omega=0.75\sim0.9$;

when the lesion is in the branch vessel, the correction parameter $\omega=0.5\sim0.85$.

The present invention further provides a method for obtaining blood vessel stress, including ts:

the above method of establishing a blood vessel cross-section function;

weighting and summing a first absolute value function of the first difference function corresponding to the two adjacent feature times at the same position according to the ratio of the time intervals between each feature time and the adjacent feature time in a cardiac cycle, so as to obtain deformation of the target region blood vessel at respective positions.

Further, the method including:

Obtaining a deformation difference function between the deformations corresponding to the target region blood vessels at two adjacent positions according to the deformations the target region blood vessel at each position.

Further, the method including:

summing according to the second absolute value function of the deformation difference function, so as to obtain deformation unevenness of the target region blood vessel.

The present invention further provides a device for establishing a blood vessel cross-section function, including:

an image obtaining module configured to obtain image data in at least one cardiac cycle;

a time selection module configured to select a plurality of feature times in the one cardiac cycle;

a spatial model generating module configured to generate spatial models of a target region blood vessel corresponding to each of the feature times according to the image data;

a first cross-section model establishing module configured to establish a first cross-section model of the target region blood vessel at each position along an axial direction of the target region blood vessel according to each of the spatial models; and a first cross-section function establishing module configured to establish a corresponding first cross-section function according to each first cross-section model.

Further, the device includes:

along the time sequence, the plurality of feature times are sequentially $t_1, t_2, \ldots, t_q$; along the axial direction of the target region blood vessel, the first cross-section functions corresponding to the first cross-section models at each position $1, 2, \ldots, r$ from a proximal end to a distal end of the target region blood vessel are $d_1, d_2, \ldots, d_r$; and the device further including:

a first cross-section matrix establishing module, configured to establish a first cross-section matrix A according to a correspondence relationship between the first cross-section function and the feature time and position, $$A = \begin{bmatrix} A_{11} & A_{12} & \ldots & A_{1q} \\ A_{21} & A_{22} & \ldots & A_{2q} \\ \vdots & \vdots & \vdots & \vdots \\ A_{r1} & A_{r2} & \ldots & A_{rq} \end{bmatrix}$$

wherein, $A_{rq}$ is the first cross-section function $d_r$ corresponding to the first cross-section model at the feature time $t_q$, at the position r of the target region blood vessel; q=r or q≠r, and q and r are positive integers.

Further, the device further includes:

a first difference function establishing module configured to establish a first difference function between the first cross-section functions corresponding to the two adjacent positions of the target region blood vessels at each feature time, along a column direction, according to the first cross-section matrix A.

Further, the device further includes:

a first variation function establishing module configured to establish, according to the first difference function, a first variation function f(x) of the target region blood vessel at each feature time that is changed with a distance x from any position to a reference point. Further, the first cross-section model includes a second cross-section model at different scales, and the device further includes:

a second cross-section function establishing module, configured to establish a corresponding second cross-section function according to the second cross-section model at each scale; and a second cross-section matrix establishing module, configured to establish a second cross-section matrix at different scales according to a correspondence relationship between the second cross-section function and the feature time and position, wherein, the scale is the distance between two adjacent positions.

Further, the scale includes a first scale, a second scale, ..., an $n^{th}$ scale, and the device further includes:

a second difference function establishing module, configured to establish, according to the second cross-section matrix at each scale, a second difference function between the second cross-section functions corresponding to two adjacent positions of the target region blood vessel at different scales in a column direction; and a second change function establishing module, configured to establish, according to the second difference function at the first scale, the second scale, ..., the $n^{th}$ scale, a second variation function $f_1(x), f_2(x), \ldots, f_n(x)$ of the corresponding target region blood vessel that is changed with a distance x from any position to the reference point, wherein, n is a positive integer greater than a.

Further, the device further includes:

a first difference function establishing module, configured to establish, according to the first cross-section matrix A, a first difference function between the first cross-section functions corresponding to the two adjacent feature times of the target region blood vessel at each position along a row direction.

Further, the first cross-section function includes one or more of the following: an area function, a diameter function, a perimeter function, and an edge distance function.

The present invention further provides a device for obtaining a blood vessel pressure difference, including:

the above device for establishing a blood vessel cross-section function;

a blood flow model obtaining module, configured to obtain a blood flow model of the target region blood vessel according to the image data;

a blood flow velocity obtaining module, configured to obtain a blood flow velocity V of the target region blood vessel according to the blood flow model;

a first blood vessel pressure difference obtaining module, configured to obtain a first blood vessel pressure difference $\Delta p_1$ at each feature time according to the blood flow velocity V and the second variation function $f_1(x), f_2(x), \ldots f_n(x)$; and a second blood vessel pressure difference obtaining module, configured to weight and sum the first blood vessel pressure difference $\Delta p_1$ according to a ratio of the time interval between each feature time and the adjacent feature time in one cardiac cycle so as to obtain a second blood vessel difference $\Delta p_2$.

Further, a calculation formula of the first blood vessel pressure difference $\Delta p_1$ at different scales is:

$$\Delta p_1 = (c_1 V + c_2 V^2 + \ldots + c_m V^m) * [\alpha_1 * \smallint\!\smallint f_1(x)dx + \alpha_2 * \smallint\!\smallint f_2(x)dx + \ldots + \alpha_n * \smallint\!\smallint f_n(x)dx], \text{where,}$$

$c_1, c_2, \ldots, c_m$ are reference coefficients of blood flow velocity V, respectively;

$\alpha_1, \alpha_2, \ldots, \alpha_n$ are weighting coefficients of the second variation function $f_1(x), f_2(x), \ldots, f_n(x)$ at different scales, respectively;

m, n are positive integers.

Further, the device further includes:

a regional information obtaining module, configured to obtain, according to each spatial model, regional information of a coronary artery system where a lesion is located;

a third blood vessel pressure difference obtaining module, configured to correct the first blood vessel pressure difference $\Delta p_1$ according to the regional information, so as to obtain a corrected third blood vessel pressure difference $\Delta p_3$, wherein, the third blood vessel pressure difference $\Delta p_3$ and the first blood vessel pressure difference $\Delta p_1$ satisfy the following relationship:

$$\Delta p_3 = \omega * \Delta p_1, \omega \text{ is a correction parameter}, 0.5 \le \omega \le 1.$$

Further, the regional information includes one or more of the following: a left main artery, a left anterior descending artery, a left circumflex artery, a right coronary artery, and a branch vessel.

Further, the correction parameter w satisfies one or more of the following:

when the lesion is in the left main artery, the correction parameter $\omega = 1$;

when the lesion is in the left anterior descending artery, the correction parameter $\omega = 0.9\sim1.0$;

when the lesion is in the left circumflex artery, the correction parameter $\omega = 0.65\sim0.85$;

when the lesion is in the right coronary artery, the correction parameter $\omega = 0.75\sim0.9$;

when the lesion is in the branch vessel, the correction parameter $\omega = 0.5\sim0.85$.

The present invention further provides a device for obtaining blood vessel stress, including:

the above device for establishing a blood vessel cross-section function;

a deformation obtaining module configured to weight and sum a first absolute value function of the first difference function corresponding to the two adjacent feature times at the same position according to the ratio of the time intervals between each feature time and the adjacent feature time in a cardiac cycle, so as to obtain deformations of the target region blood vessel at each position.

Further, the device further includes:

a deformation difference function obtaining module configured to obtain a deformation difference function between the deformations corresponding to the target region blood vessels at two adjacent positions according to the deformations the target region blood vessel at each position.

Further, the device further includes:

a deformation unevenness obtaining module configured to sum according to the second absolute value function of the deformation difference function, so as to obtain deformation unevenness of the target region blood vessel.

Therefore, the method for establishing a blood vessel cross-section function provided by the present invention is based on blood vessel cross-section functions established at different positions and at different times. Compared with the blood vessel cross-section functions established based on only space or only time in the prior art, the present invention can more accurately reflect the actual conditions of blood vessels, and provides an intermediate variable with less error for subsequent analysis operations, so that the later calculated value is closer to the actual value.

To make the above content of the present invention more obvious and comprehensible, preferred embodiments are described in detail below with reference to the drawings.

BRIEF DESCRIPTION OF THE DRAWINGS

Specific embodiments of the present invention will be further described in detail below with reference to the accompanying drawings.

DETAILED DESCRIPTION

The embodiments of the present invention are described below by way of specific embodiments, and those skilled in the art can readily understand other advantages and functions of the present invention from the disclosure of the present disclosure. Although the description of the present invention will be described in conjunction with the preferred embodiments, this is not a limitation of the invention. Rather, the invention is described in connection with the embodiments so as to cover other alternatives or modifications that are possible in the embodiments of the invention. In order to provide a thorough understanding of the present invention, many specific details are included in the following description. The invention may also be practiced without these details. In addition, some specific details are omitted in the description in order to avoid obscuring or obscuring the present invention. It should be noted that the embodiments in the present invention and the features in the embodiments may be combined with each other without conflict.

Figure 1:
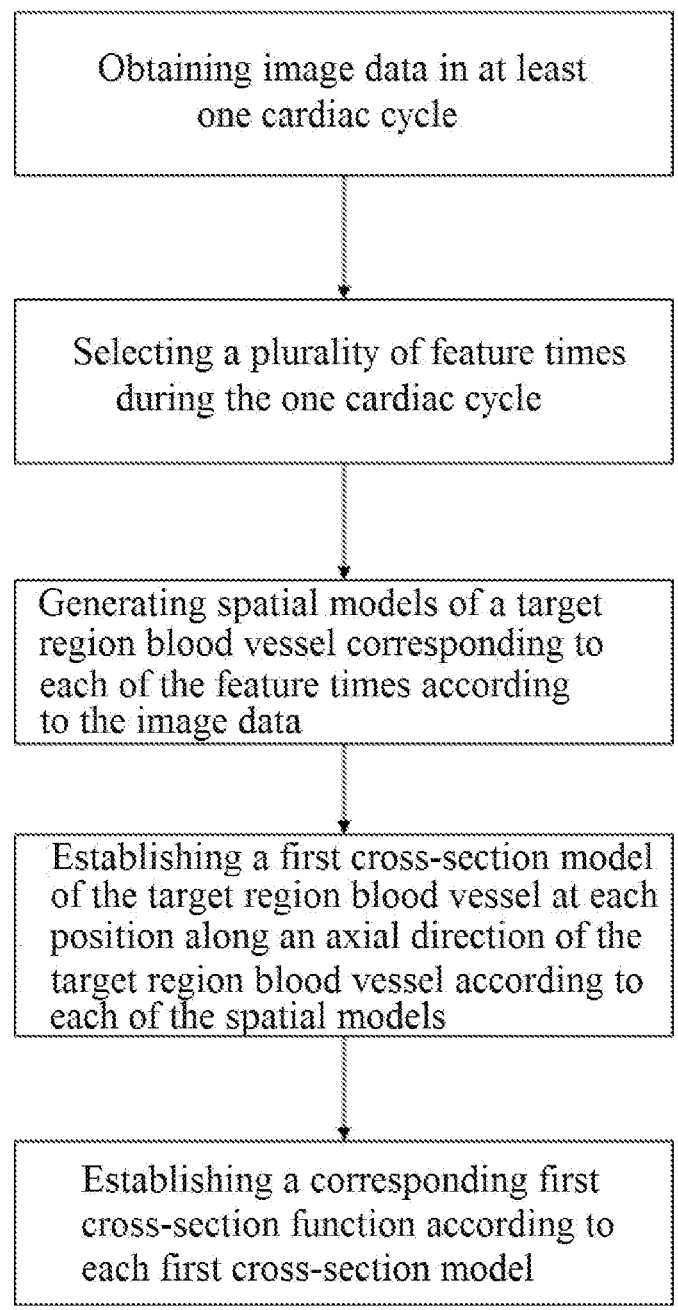
FIG. 1 is a schematic flow chart of a method for establishing a blood vessel cross-section function according to an embodiment of the present invention.

Referring to FIG. 1, the present invention provides a method of establishing a blood vessel cross-section function comprising the following steps:

obtaining image data in at least one cardiac cycle;

selecting a plurality of feature times during the one cardiac cycle;

generating spatial models of a target region blood vessel corresponding to each of the feature times according to the image data;

establishing a first cross-section model of the target region blood vessel at each position along an axial direction of the target region blood vessel according to each of the spatial models;

establishing a corresponding first cross-section function according to each first cross-section model.

It should be noted that the "feature time" may be each time point corresponding to each image data in which the image data is clear and convenient for analysis in the image data of one cardiac cycle. In the case of a diseased blood vessel, the "target region blood vessel" may be a blood vessel in a certain region including at least the diseased blood vessel. The "each position" may be a position which is continuously obtained at a minimum interval corresponding to a resolution in the axial direction based on the resolution of the obtained image data. The "first cross-section function" may be all physical quantity function capable of reflecting the cross-section forms of the target region blood vessel (lumen cross-section form) and capable of being calculated.

In an embodiment, image data can be acquired by means of detection such as CT, OCT, IVUS, and X-ray. The spatial model includes at least the following parameters: shape, length, diameter, and area of the target region blood vessel. The spatial model can be multi-dimensional, such as two-dimensional, three-dimensional, etc., and the maximum achievable dimension is limited by the detection means used to obtain the image data.

For blood vessels, at the same time point, due to the different degrees of contraction and relaxation at various locations, the lumen form is different. In particular, for a blood vessel in which a lesion occurs, such as a plaque having blood vessel, at the same time point, the lumen forms of the blood vessel at the plaque position and the blood vessel at the position without the plaque, are not the same. Even in the same blood vessel having plaque, at the same time, the lumen form at each position is different. Similarly, for the blood vessels at the same location, the lumen form at different points in time is also different.

Therefore, the method for establishing a blood vessel cross-section function provided by the present invention is based on a blood vessel cross-sectional function established at different positions and at different times. And compared to a blood vessel cross-section function established only based on space or only based on time in the prior art, it can more accurately reflect the actual condition of the blood vessel, and provides an intermediate variable with less error for the subsequent analysis operation, so that the later calculated value is closer to the actual value.

In this embodiment, the first cross-section model can be established by following steps: the cross-section of the proximal end of the target region blood vessel is used as a reference surface, and an intercross-section point of the reference surface and the central axis of the spatial model of the target region blood vessel is used as a reference point; the reference point is used as an origin, a direction extending along the central axis is an x-axis, and a coordinate system is established; cross-sections of target region blood vessel at each position are obtained along a direction of its vertical central axis, and the inner and outer edges of each cross-section are projected into the coordinate system to obtain planar geometry of the lumen cross-section at each location of the blood vessel of the target region. That is, the first cross-section model is established. In other embodiments, the first cross-section model can also be established by other methods of coordinate creation and projection.

It should be noted that the "proximal end" of the present application is one end of the blood vessel in the target region where the blood flow flows through first; and the "distal end" is one end of the blood vessel of the target region where the blood flow flows through later.

Further, the method of establishing a blood vessel cross-section function further comprises the following steps:

Along time series, the plurality of feature times are sequentially $t_1, t_2, \ldots, t_q$; along the axial direction of the target region blood vessel, the first cross-section functions corresponding to the first cross-section models at each position $1, 2, \ldots, r$ from a proximal end to a distal end of the target region blood vessel are $d_1, d_2, \ldots, d_r$:

Establishing a first cross-section matrix A according to a correspondence relationship between the first cross-section function, and the feature time and position, $$A = \begin{bmatrix} A_{11} & A_{12} & \ldots & A_{1q} \\ A_{21} & A_{22} & \ldots & A_{2q} \\ \vdots & \vdots & \vdots & \vdots \\ A_{r1} & A_{r2} & \ldots & A_{rq} \end{bmatrix}$$

Wherein, $A_{rq}$ is the first cross-section function $d_r$ corresponding to the first cross-section model at the feature time $t_q$, at the position r of the target region blood vessel; q=r or q≠r, and q, r are positive integer.

In this embodiment, the first cross-section function includes one or more of the following: an area function, a diameter function, a perimeter function, and an edge distance function. It should be noted that the area function may be a function representing the cross-sectional area of the lumen. The perimeter function can be a function representing a circumference of the lumen's cross-section. The diameter function can be a function representing a diameter of the lumen's cross-section, where the diameter can be a diameter of the lumen's cross-section that is strictly geometrically circular, or an equivalent diameter of the lumen's cross-section that is not strictly geometrically circular.

The edge distance function can be understood as: at the same feature time, each point on the cross-section edge at a certain position is corresponding to each point on the cross-section edge at another adjacent position, calculate the direct or indirect distance between the corresponding points on the edges of the two cross-sections, and then obtained by summing or averaging. Alternatively, at the same position, each point on the cross-section edge corresponding to a certain feature time corresponds to each point on the cross-section edge of corresponding to another adjacent feature time, and the direct or indirect distance between the corresponding points on the edges of the two cross-sections is calculated, and then obtained by summing or averaging.

It should be noted that the direct distance can be understood as: ignoring the distance between the two cross-sections in the axial direction by overlapping the two cross-sections with each other, and directly calculating the distance between the corresponding points on the two cross-section edges. If the direct distance between the corresponding points on the two cross-sections is 0, that is, the edge distance function of both cross-sections is 0, then the lumen forms represented by the two cross-sections are exactly identical; if not, the lumen forms represented by the two cross-sections are not exactly identical. The lumen forms being exactly identical can be understood that the inner and outer contours of the two lumens at the corresponding points can completely overlap.

The indirect distance can be understood as: by introducing a reference position, calculating the distance of each point on the edge of the two cross-sections from the reference position. For example, the reference position may be the central axis position of the spatial model of the target region blood vessel. If the indirect distance of each point on the two cross-section edge from the central axis is a certain fixed value, that is, the edge distance functions of the two cross-sections are both a certain fixed value, then the lumen forms represented by the two cross-sections are exactly the same; if not, the lumen forms represented by the two cross-sections are not exactly the same.

Further, the method of establishing a blood vessel cross-section function further comprises:

It establishes a first difference function between the first cross-section functions corresponding to the two adjacent positions of the target region blood vessels at each feature time, along a column direction, according to the first cross-section matrix A.

Further, the method of establishing a blood vessel cross-section function further comprises: According to the first difference function, it establishes a first variation function f(x) of the target region blood vessel at each feature time that is changed with a distance x from the reference point to any position thereof.

Wherein, the reference point is the intercross-section of the central axis of the spatial model of the target region blood vessel and the reference surface, wherein, the cross-section of the proximal end of the target region blood vessel is used as the reference surface.

The first difference function can represent a function of the difference between lumen forms represented by the cross-cross-sections at two adjacent locations. In this embodiment, the first cross-section function is a constant value function. The first difference function obtained by the first cross-section function calculation is also a constant value function. The first variation function f(x) can be obtained by data fitting a plurality of pairs of discrete points composed of the first difference function and the corresponding distance x.

Figure 2:
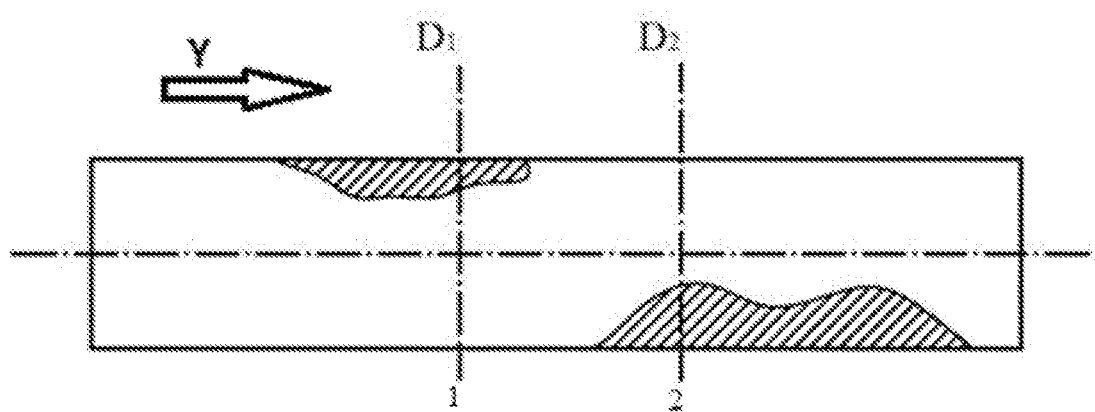
FIG. 2 is a schematic view showing a spatial model of a target blood vessel in a form according to an embodiment of the present invention.
Figure 3:
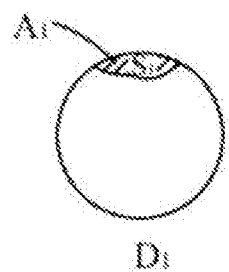
FIG. 3 is a schematic structural view of the first cross-section model D1 of FIG. 2.
Figure 4:
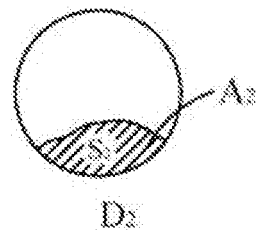
FIG. 4 is a schematic structural view of the first cross-section model D2 of FIG. 2.
Figure 5:
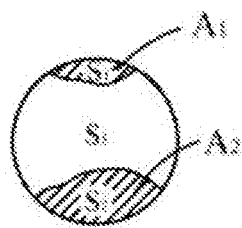
FIG. 5 is a schematic structural view of the first cross-section model D1 and the first cross-section model D2 in FIG. 3 and FIG. 4 overlapping each other at a corresponding point.

Specifically, refer to FIG. 2, blood in the target region blood vessel flows in the blood flow direction Y. When the first cross-section function is an area function, each point on the cross-section edge of the target region blood vessel at position 1 and position 2 is in one-to-one correspondence. Referring to FIG. 3, the first cross-section model $D_1$ of the target region blood vessel at the position 1 has a plaque region of $A_1$, and the corresponding area is $S_1$. Referring to FIG. 4, the first cross-section model $D_2$ of the target region blood vessel at the position 2 has a plaque region of $A_2$, and a corresponding area of $S_2$. Referring to FIG. 5, since the lumens (plaques) of $D_1$ and $D_2$ do not overlap, the blood flow pressure will change as the blood flows through $D_1$ to $D_2$. At this time, the first difference function is the ratio of the non-overlapping regions ($S_1$, $S_2$) to the overlapping region area ($S_3$) in the two cross-sections; or the ratio of the non-overlapping region ($S_1$, $S_2$) to the total area ($S_1$, $S_2$, $S_3$), and the first variation function f(x)>0, that is, there is a pressure difference between $D_1$ and $D_2$.

Figure 6:
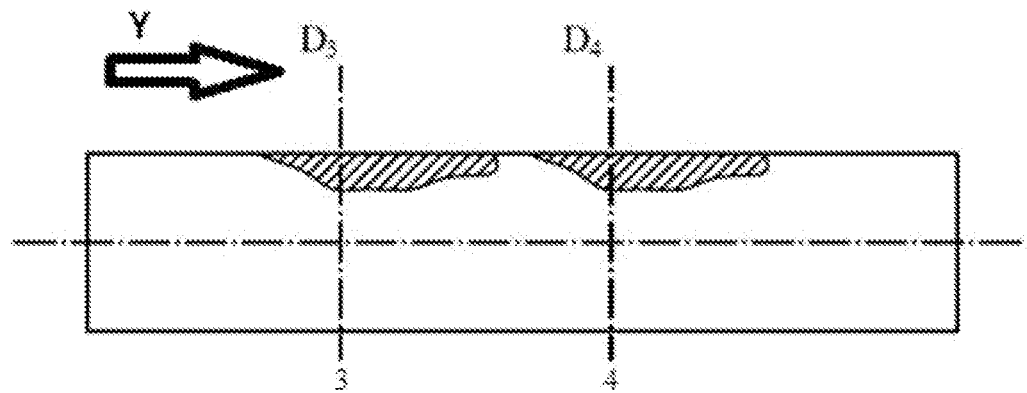
FIG. 6 is a schematic view showing a spatial model of a target blood vessel in another form according to an embodiment of the present invention.
Figure 7:
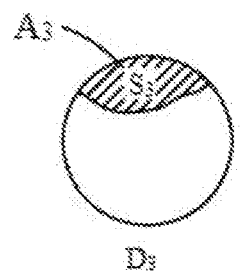
FIG. 7 is a schematic structural view of the first cross-section model D3 of FIG. 6.
Figure 8:
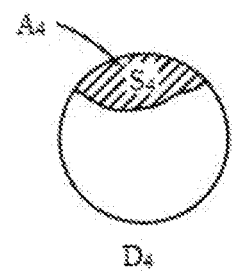
FIG. 8 is a schematic structural view of the first cross-section model D4 of FIG. 6.
Figure 9:
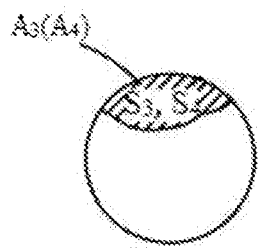
FIG. 9 is a schematic structural view of the first cross-section model D3 and the first cross-section model D4 in FIG. 7 and FIG. 8 overlapping each other at a corresponding point.

Referring to FIG. 6, blood in the target region blood vessel flows in the blood flow direction Y. Referring to FIG. 7, a first cross-section model $D_3$ of the target region blood vessel at a position 3 has a plaque region of $A_3$, and the corresponding area is $S_3$. Referring to FIG. 8, a first cross-section model $D_4$ of the target region blood vessel at a position 4 has a plaque region of $A_4$, and the corresponding area is $S_4$. Where $S_4=S_3$. Referring to FIG. 9, the plaque regions $A_3$ and $A_4$ can completely overlap, that is, the non-overlapping regions ($S_3$, $S_4$)=0, the first difference function is 0, and the first variation function f(x)=0, that is, there is no pressure difference between $D_3$ and $D_4$.

Similarly, when the first cross-section function is an edge distance function, the first variation function f(x)≠0 between $D_1$ and $D_2$, that is, the two lumen forms do not completely overlap, and there is a pressure difference between $D_1$ and $D_2$. The first variation function f(x)=0 between $D_3$ and $D_4$, that is, the two lumen forms completely overlap, and there is no pressure difference between $D_3$ and $D_4$.

The first difference function is a function between the first cross-section functions corresponding to two adjacent positions of the target region blood vessels at each feature time along a column direction according to the first cross-section matrix A; or, is a function between the first cross-section functions corresponding to the two adjacent feature times of the target region blood vessels at each position along a row direction according to the first cross-section matrix A.

That is to say, the first difference function can be obtained by calculating in two different path, (1) along the column direction; (2) along the row direction. In other embodiments, the first difference function may also be obtained by calculating in other path, such as in a diagonal direction. The first difference function obtained by calculating in different paths may be the same or different. Specifically, an appropriate path can be selected according to the calculation amount finally required to be obtained, such as a blood vessel pressure difference, a blood flow reserve fraction, a blood vessel stress, and the like.

In this embodiment, when the calculated amount to be finally obtained is a blood vessel pressure difference or a blood flow reserve fraction, the first difference function may be obtained by calculating in the first cross-section matrix A, along the column direction, that is, along a direction whose feature times are the same and the positions are different. When the calculated amount to be finally obtained is a blood vessel stress, the first difference function can be obtained by calculating in the first cross-section matrix A, along the row direction, that is, along a direction whose positions are the same and the feature times are different.

Further, the first cross-section model includes a second cross-section model at different scales.

The method of establishing a blood vessel cross-section function further includes:

Establishing a corresponding second cross-section function according to the second cross-section model at each scale;

According to the correspondence relationship between the second cross-section function and the feature time and position, a second cross-section matrix at different scales is established, Wherein, the scale is the distance between two adjacent positions.

Further, the scale includes a first scale, a second scale, . . . , an nth scale.

The method of establishing a blood vessel cross-section function further includes: establishing a second difference function between the second cross-section functions corresponding to two adjacent positions of the target region blood vessels at different scales, along the column direction, according to the second cross-section matrix at each scale; establishing a second variation function $f_1(x)$, $f_2(x)$, . . . , $f_n(x)$ of the corresponding target region blood vessel that is changed with a distance x from its any position to the reference point, according to the second difference function at the first scale, the second scale, . . . , the nth scale.

Wherein n is a positive integer greater than 1.

The first scale, the second scale, . . . , the nth scale may be used to detect different lesion features. For example, the first lesion feature needs to be detected with a larger scale of the first scale; the nth lesion feature needs to be detected with a smaller scale of the nth scale. With different scales, various lesions can be detected more accurately, and the error between the calculated result and the actual value can be further reduced.

The invention also provides a method for obtaining a blood vessel pressure difference, comprising the following steps:

The above method of establishing a blood vessel cross-section function;

Obtaining a blood flow model of a target region blood vessel according to image data;

Obtaining a blood flow velocity V of a target region blood vessel according to the blood flow model;

Obtaining a first blood vessel pressure difference $\Delta p_1$ at each feature time according to a blood flow velocity V and a second variation function $f_1(x)$, $f_2(x)$, . . . , $f_n(x)$;

The first blood vessel pressure difference $\Delta p_1$ is weighted and summed according to a ratio of the time interval between each feature time and the adjacent feature time in one cardiac cycle, so as to obtain the second blood vessel pressure difference $\Delta p_2$.

The ratio of the time interval between each feature time and the adjacent feature time in one cardiac cycle means, for example, selecting four feature times within one cardiac cycle, and sequentially $t_1$, $t_2$, $t_3$, $t_4$ along the time sequence. A cardiac cycle is T, then a ratio of $t_1$ in one $$\text{cardiac cycle} = \frac{t_2 - t_1}{T};$$

a ratio of $t_2$ in one $$\text{cardiac cycle} = \frac{t_3 - t_2}{T},$$

and so on. Alternatively, a ratio of $t_2$ in one $$\text{cardiac cycle} = \frac{t_2 - t_1}{T};$$

a ratio of $t_3$ in one $$\text{cardiac cycle} = \frac{t_3 - t_2}{T},$$

and so on. Alternatively, a ratio of $t_1$ in one $$\text{cardiac cycle} = \frac{\frac{1}{2}(t_2 - t_1) + \frac{1}{2}(t_3 - t_2)}{T};$$

a ratio of $t_2$ in one $$\text{cardiac cycle} = \frac{\frac{1}{2}(t_3 - t_2) + \frac{1}{2}(t_4 - t_3)}{T},$$

and so on.

The blood flow model includes a fixed blood flow model and a personalized blood flow model. The fixed blood flow model is an empirical value blood flow model, which is directly established by the method of big data collection and simulation based on clinical practical experience. The blood flow velocity V can be obtained directly from the fixed blood flow model. The blood flow velocity V can be a fixed value.

The personalized blood flow model further includes a resting state blood flow model and a load state blood flow model. When the personalized blood flow model is the resting state blood flow model, the blood flow velocity V can be obtained by calculating the velocity in the fluid filling state.

In one embodiment, the resting state blood flow model is a contrast agent blood flow model. The blood flow velocity V can be obtained by using a grayscale time fitting function, so as to obtain the average blood flow velocity $V_{qc}$ of the contrast agent in the target region blood vessel during the contrast process; or, it can be calculated by using the TIMI number frame method, so as to obtain the mean blood flow velocity of the agent $V_{qc}$ of the target region blood vessel during the contrast process.

In another embodiment, the resting state blood flow model is a CT blood flow model. The blood flow velocity V can be obtained by calculation of the morphology of the blood vessel tree. The morphology of the vascular tree includes at least one or more of the following: the area and volume of the blood vessel tree and the lumen diameter of the blood vessel segment in the blood vessel tree. The spatial model also needs to include at least one or more of the following parameters: perfusion area and branch vessel angle.

When the personalized blood flow model is a load state blood flow model, the blood flow velocity V is the maximum blood flow velocity $V_{max}$ after the blood flow is fully expanded by injecting adenosine.

In general, when the target region blood vessel is located in the coronary region, the blood flow velocity V is the maximum blood flow velocity $V_{max}$; when the target region blood vessel is located in the peripheral blood vessel system, the blood flow velocity V is the average blood flow velocity $V_{qc}$ in the resting state.

Wherein, a calculation formula of the first blood vessel pressure difference $\Delta p_1$ at different scales is:

$$\Delta p_1 = (c_1 V + c_2 V^2 + \ldots + c_m V^m) * [\alpha_1 * \smallint\smallint f_1(x) dx + \alpha_2 * \smallint\smallint f_2(x) dx + \ldots + \alpha_n * \smallint\smallint f_n(x) dx], \text{ wherein,}$$

$c_1, c_2, \ldots, c_m$ are reference coefficients of blood flow velocity V, respectively;

$\alpha_1, \alpha_2, \ldots, \alpha_n$ are weighting coefficients of the second variation function $f_1(x), f_2(x), \ldots, f_n(x)$ at different scales, respectively;

m, n are positive integers.

Wherein, the reference coefficients $c_1, c_2, \ldots, c_m$ include a plurality of parameter coefficients such as blood viscosity influencing factors, blood turbulence influencing factors and viscosity coefficients. In the present embodiment, m=2, and $c_1$ is a parameter coefficient due to blood flow friction, and $c_2$ is a parameter coefficient generated by blood turbulence.

Further, the method for obtaining a blood vessel pressure difference further includes: Obtaining regional information of the coronary system where the lesion is located according to each spatial model;

Correcting the first blood vessel pressure difference $\Delta p_1$ according to the regional information, so as to obtain the corrected third blood vessel pressure difference $\Delta p_3$, wherein, the third blood vessel pressure difference $\Delta p_3$ and the first blood vessel pressure difference $\Delta p_1$ satisfy the following relationship:

$\Delta p_3 = \omega * \Delta p_1$, $\omega$ is a correction parameter, and $0.5 \leq \omega \leq 1$.

Due to the different positions of the lesions (plaques), the myocardial volume regions supplied by the target region blood vessels are different, and thus the calculated value of the blood vessel pressure difference in the target region may be deviated. Therefore, the present invention reduces the influence of the positional factor of the lesion (plaque) on the calculation of the pressure difference by introducing the correction parameter w, and improves the accuracy of the calculation result.

In the present embodiment, the regional information includes one or more of the following: a left main artery, a left anterior descending artery, a left circumflex artery, a right coronary artery, and a branch vessel.

The correction parameter w satisfies one or more of the following:

When the lesion is in the left main trunk, the correction parameter $\omega=1$;

When the lesion is in the left anterior descending artery, the correction parameter $\omega=0.9\sim1.0$;

When the lesion is in the left circumflex artery, the correction parameter $\omega=0.65\sim0.85$;

When the lesion is in the right coronary artery, the correction parameter $\omega=0.75\sim0.9$;

When the lesion is in the branch vessel, the correction parameter $\omega=0.5\sim0.85$.

It should be noted that, besides the positional factors of the above lesions (plaques) may affect the calculation results of the blood vessel pressure difference in the target region, other medical history information and physiological information may also affect the pressure difference calculation results in different degrees. In other embodiments, the medical history information and the physiological information may also be subjected to a deviation elimination process. Wherein, the medical history information includes: circulatory diseases, respiratory diseases, nervous system diseases, bone diseases, digestive diseases, metabolic diseases and family history that affect blood flow velocity or blood viscosity. Physiological information includes information such as age, gender, blood pressure, body mass index, and coronary artery superiority that can be obtained directly or indirectly.

Based on the pressure difference obtained by the above method, the blood flow reserve fraction FFR can be further obtained by calculating.

The method of obtaining the blood flow reserve fraction FFR includes at least the following steps:

Obtaining the pressure value $p_a$ of the proximal end of the target region blood vessel;

According to the proximal pressure value $p_a$ and the second blood vessel pressure difference $\Delta p_2$, the blood flow reserve fraction FFR is obtained, Wherein, the blood flow reserve fraction FFR satisfies the following formula:

$$FFR = \frac{p_a - \Delta p_2}{p_a}$$

The invention also provides a method for acquiring blood vessel stress, comprising:

Establishing a blood vessel cross-section function according to the above method;

weighting and summing a first absolute value function of the first difference function corresponding to the two adjacent feature times at the same position according to the ratio of the time intervals between each feature time and the adjacent feature time in a cardiac cycle, so as to obtain deformations of the target region blood vessel at each position.

It should be noted that the first difference function is obtained by calculating in the row direction, that is, in a direction in which the position is the same and the feature time is different, in the first cross-section matrix A. The first absolute value function is a function obtained by taking the absolute value of the first difference function.

Further, the method for acquiring blood vessel stress further includes the following steps:

obtaining a deformation difference function between the deformations corresponding to the target region blood vessels at two adjacent positions according to the deformations the target region blood vessel at each position.

Further, the method for acquiring blood vessel stress further includes the following steps:

summing according to the second absolute value function of the deformation difference function, so as to obtain deformation unevenness of the target region blood vessel.

It should be noted that the second absolute value function is a function obtained by taking an absolute value of the deformation difference function.

The stress obtained by the above method is closer to the actual value than the stress calculated in the prior art based only on time or based only on space, and thus the accuracy of subsequent evaluation and decision making can be improved. For example, it evaluates the real-time deformability and mechanical behavior of normal or diseased vessel walls, evaluates the risk of plaque rupture in normal or diseased vessel walls, and evaluates the location of the stent and displacement of the lesion plaque in the cardiac cycle during stent intervention, the effect on lumen anatomy, and the potential risk of stent fracture.

Figure 10:
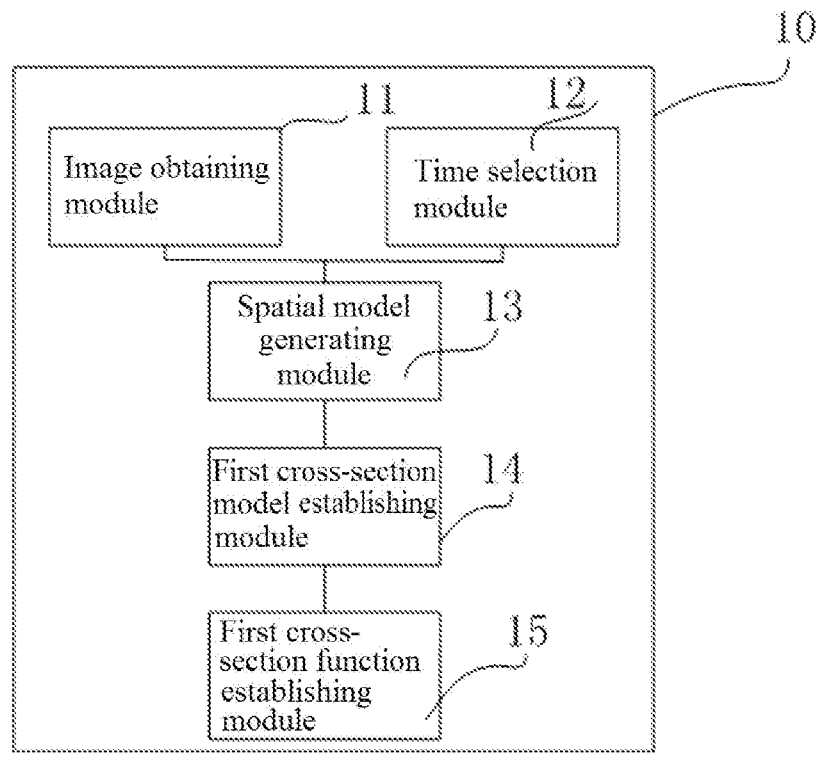
FIG. 10 is a schematic structural view of a device for establishing a blood vessel cross-section function according to an embodiment of the present invention.

Referring to FIG. 10, the present invention also provides a device 10 for establishing a blood vessel cross-section function, comprising:

an image obtaining module 11 configured to obtain image data within at least one cardiac cycle;

a time selection module 12 configured to select a plurality of feature times in the one cardiac cycle;

a spatial model generating module 13 configured to generate spatial models of a target region blood vessel corresponding to each of the feature times according to the image data;

a first cross-section model establishing module 14 configured to establish a first cross-section model of the target region blood vessel at each position along an axial direction of the target region blood vessel according to each of the spatial models;

a first cross-section function establishing module 15 configured to establish a corresponding first cross-section function according to each first cross-section model.

Further, the device 10 for establishing a blood vessel cross-section function further comprises:

Along the time series, the plurality of feature times are sequentially $t_1, t_2, \ldots, t_q$; along the axial direction of the target region blood vessel, the first cross-section functions corresponding to the first cross-section models at each position $1, 2, \ldots, r$ from a proximal end to a distal end of the target region blood vessel are $d_1, d_2, \ldots, d_r$;

a first cross-section matrix establishing module configured to establish a first cross-section matrix A according to a correspondence relationship between the first cross-section function and the feature time and position, $$A = \begin{bmatrix} A_{11} & A_{12} & \ldots & A_{1q} \\ A_{21} & A_{22} & \ldots & A_{2q} \\ \vdots & \vdots & \vdots & \vdots \\ A_{r1} & A_{r2} & \ldots & A_{rq} \end{bmatrix}$$

Wherein, $A_{rq}$ is the first cross-section function $d_r$ corresponding to the first cross-section model at the feature time $t_q$, at the position r of the target region blood vessel; q=r or q≠r, and q, r are positive integers.

Further, the device 10 for establishing a blood vessel cross-section function further comprises: a first difference function establishing module configured to establish a first difference function between the first cross-section functions corresponding to the two adjacent positions of the target region blood vessels at each feature time, along a column direction, according to the first cross-section matrix A. Alternatively, in a row direction, a first difference function between the first cross-section functions corresponding to the two adjacent feature times of the target region blood vessel at each position is established.

Further, the device 10 for establishing a blood vessel cross-section function further comprises: a first variation function establishing module configured to establish, according to the first difference function, a first variation function f(x) of the target region blood vessel at each feature time that is changed with a distance x from any position to a reference point.

Further, the first cross-section model includes a second cross-section model at different scales.

The device 10 for establishing a blood vessel cross-section function further includes:

a second cross-section function establishing module, configured to establish a corresponding second cross-section function according to the second cross-section model at each scale;

a second cross-section matrix establishing module, configured to establish a second cross-section matrix at different scales according to a correspondence relationship between the second cross-section function and the feature time and position, Wherein, the scale is the distance between two adjacent positions.

Further, the scale includes a first scale, a second scale, . . . , an nth scale.

The device 10 for establishing a blood vessel cross-section function further includes:

a second difference function establishing module configured to establish, according to the second cross-section matrix at each scale, a second cross-section function between the second cross-section functions corresponding to two adjacent positions of the target region blood vessel at different scales in a column direction;

a second change function establishing module configured to establish, according to the second difference function at the first scale, the second scale, . . . , the nth scale, a second variation function $f_1(x), f_2(x), \ldots, f_n(x)$ of the corresponding target region blood vessel that is changed with a distance x from any position to the reference point, Where n is a positive integer greater than 1.

Figure 11:
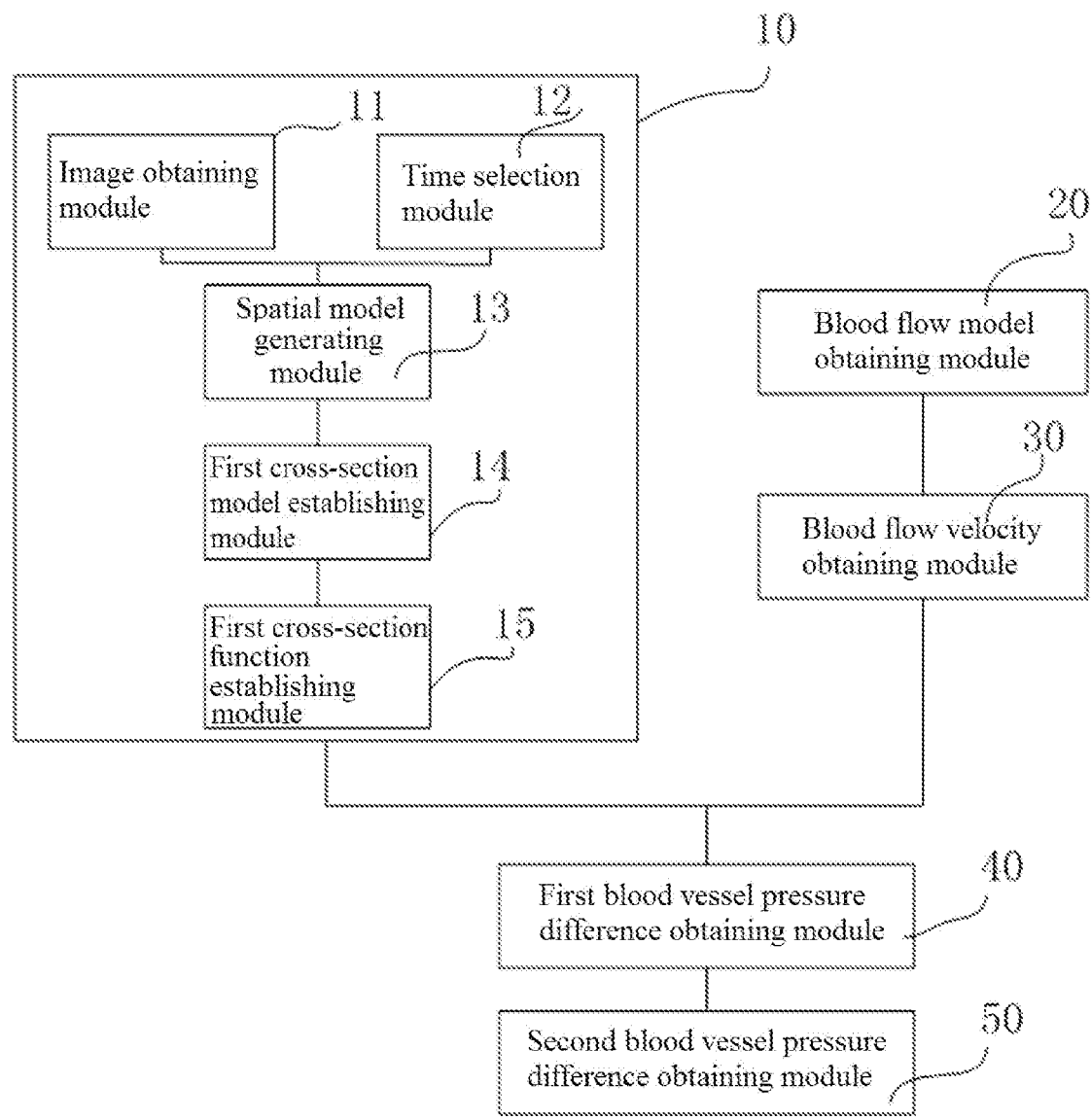
FIG. 11 is a schematic structural view of a device for acquiring a blood vessel pressure difference according to an embodiment of the present invention.

Referring to FIG. 11, the present invention also provides a device for obtaining a blood vessel pressure difference, comprising:

the above device 10 for establishing a blood vessel cross-section function;

a blood flow model obtaining module 20 configured to obtain a blood flow model of the target region blood vessel according to the image data;

a blood flow velocity obtaining module 30 configured to obtain a blood flow velocity V of the target region blood vessel according to the blood flow model;

a first blood vessel pressure difference obtaining module 40 configured to obtain a first blood vessel pressure difference $\Delta p_1$ at each feature time according to the blood flow velocity V and the second variation function $f_1(x), f_2(x), \ldots, f_n(x)$;

a second blood vessel pressure difference obtaining module 50 configured to weight and sum the first blood vessel pressure difference $\Delta p_1$ according to a ratio of the time interval between each feature time and the adjacent feature time in a cardiac cycle so as to obtain a second blood vessel pressure difference $\Delta p_2$.

Further, the device for obtaining a blood vessel pressure difference further includes:

a regional information obtaining module configured to obtain, according to each spatial model, regional information of a coronary artery system where the lesion is located;

a third blood vessel pressure difference obtaining module configured to correct the first blood vessel pressure difference $\Delta p_1$ according to the regional information, so as to obtain the corrected third blood vessel pressure difference $\Delta p_3$, Wherein, the third blood vessel pressure difference $\Delta p_3$ and the first blood vessel pressure difference $\Delta p_1$ satisfy the following relationship:

$\Delta p_3 = \omega * \Delta p_1, \omega$ is a correction parameter, $0.5 \leq \omega \leq 1$.

Figure 12:
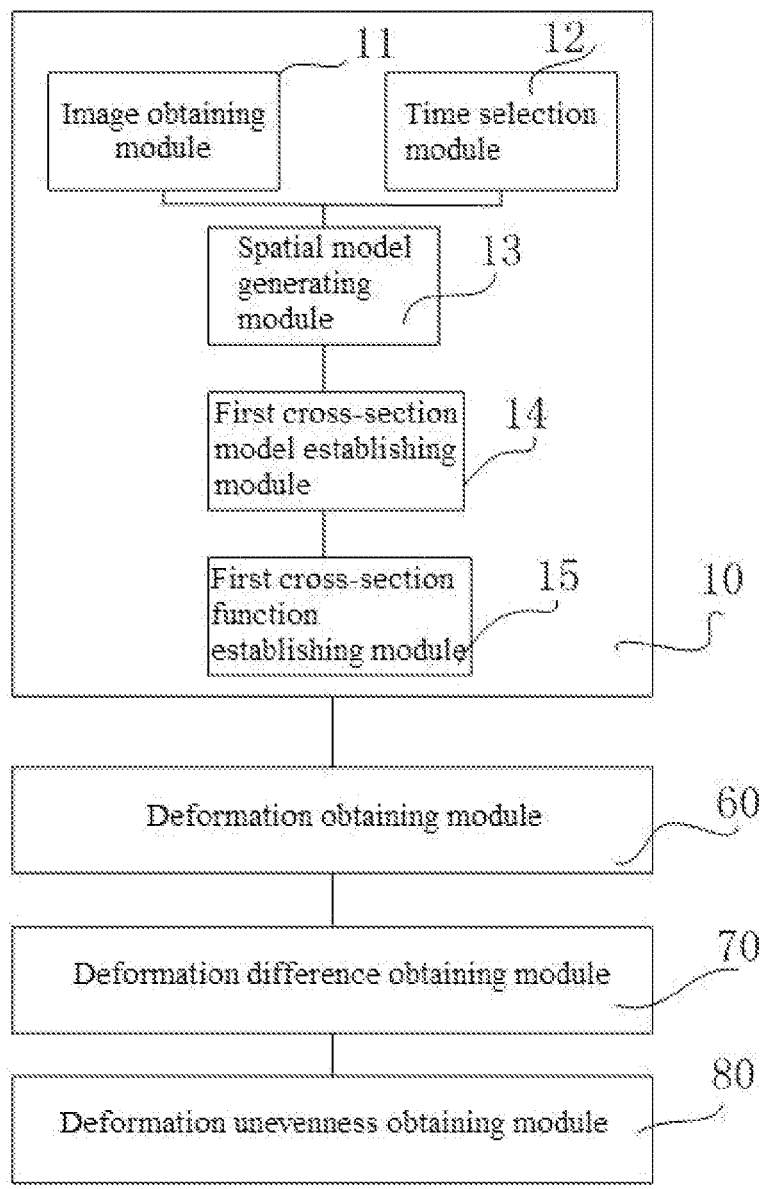
FIG. 12 is a schematic structural view of a device for acquiring blood vessel stress according to an embodiment of the present invention.

Referring to FIG. 12, the present invention also provides a device for obtaining blood vessel stress, comprising:

The above device 10 for establishing a blood vessel cross-section function;

The deformation obtaining module 60 configured to weight and sum a first absolute value function of the first difference function corresponding to the two adjacent feature times at the same position according to the ratio of the time intervals between each feature time and the adjacent feature time in a cardiac cycle, so as to obtain deformations of the target region blood vessel at each position.

Further, the device for obtaining the blood vessel stress further includes:

a deformation difference function obtaining module 70 configured to obtain a deformation difference function between the deformations corresponding to the target region blood vessels at two adjacent positions according to the deformations the target region blood vessel at each position.

Further, the device for obtaining blood vessel stress further includes:

a deformation unevenness obtaining module 80 configured to sum according to the second absolute value function of the deformation difference function, so as to obtain deformation unevenness of the target region blood vessel.

For the specific implementation of each device, please refer to the corresponding method described above, and details are not described herein again.

The above-described embodiments of the present invention are merely illustrative of the principles and effects of the present invention and are not intended to limit the present invention. Modifications or variations of the above-described embodiments may be made by those skilled in the art without departing from the spirit and scope of the invention. Therefore, all equivalent modifications or changes made by those skilled in the art without departing from the spirit and scope of the invention will be covered by the appended claims.

The invention claimed is:

1. A method for obtaining a blood vessel pressure difference, comprising:

obtaining image data in at least one cardiac cycle;

selecting a plurality of feature times during the one cardiac cycle;

generating spatial models of a target region blood vessel corresponding to each of the feature times according to the image data;

establishing a first cross-section model of the target region blood vessel at each position along an axial direction of the target region blood vessel according to each of the spatial models; and establishing a corresponding first cross-section function according to each first cross-section model;

along time series, the plurality of feature times are sequentially $t_1, t_2, \ldots, t_q$; along the axial direction of the target region blood vessel, the first cross-section functions corresponding to the first cross-section models at each position $1, 2, \ldots, r$ from a proximal end to a distal end of the target region blood vessel are $d_1, d_2, \ldots, d_r$;

establishing a first cross-section matrix A according to a correspondence relationship between the first cross-section function, and the feature time and the position, $$A = \begin{bmatrix} A_{11} & A_{12} & \ldots & A_{1q} \\ A_{21} & A_{22} & \ldots & A_{2q} \\ \vdots & \vdots & \vdots & \vdots \\ A_{r1} & A_{r2} & \ldots & A_{rq} \end{bmatrix}$$

wherein, $A_{rq}$ is the first cross-section function $d_r$ corresponding to the first cross-section model at the feature time $t_q$, at the position r of the target region blood vessel; q=r or q≠r, and q and r are positive integers;

wherein the first cross-section model includes a second cross-section model at different scales;

establishing a corresponding second cross-section function according to the second cross-section model at each scale;

according to the correspondence relationship between the second cross-section function and the feature time and position, establishing a second cross-section matrix at different scales, wherein, the scale is the distance between two adjacent positions;

the scale includes a first scale, a second scale, . . . , an $n^{th}$ scale;

establishing a second difference function between the second cross-section functions corresponding to two adjacent positions of the target region blood vessels at different scales, along the column direction, according to the second cross-section matrix at each scale; and establishing a second variation function $f_1(x)$, $f_2(x)$, . . . ,$f_n(x)$ of the corresponding target region blood vessel that is changed with a distance x from its any position to the reference point, according to the second difference function at the first scale, the second scale, . . . , the $n^{th}$ scale;

wherein, n is a positive integer greater than 1;

obtaining a blood flow model of the target region blood vessel according to image data;

obtaining a blood flow velocity V of the target region blood vessel according to the blood flow model;

obtaining a first blood vessel pressure difference $\Delta p_1$ at each feature time according to the blood flow velocity V and the second variation function $f_1(x)$, $f_2(x)$, . . . ,$f_n(x)$; and weighting and summing the first blood vessel pressure difference $\Delta p_1$ according to a ratio of a time interval between each feature time and the adjacent feature time in one cardiac cycle, so as to obtain a second blood vessel pressure difference $\Delta p_2$.

2. The method for obtaining a blood vessel pressure difference according to claim 1, wherein a calculation formula of the first blood vessel pressure difference $\Delta p_1$ at different scales is:

$$\Delta p_1 = (c_1 V + c_2 V^2 + \ldots + c_m V^m) * [\alpha_1 * \int\int f_1(x)dx + \alpha_2 * \int\int f_2(x)dx + \ldots + \alpha_n * \int\int f_n(x)dx], \text{ wherein}$$

$c_1, c_2, \ldots, c_m$ are reference coefficients of blood flow velocity V, respectively;

$\alpha_1, \alpha_2, \ldots, \alpha_n$ are weighting coefficients of the second variation function $f_1(x), f_2(x), \ldots, f_n(x)$ at different scales, respectively;

m, n are positive integers.

3. The method for obtaining a blood vessel pressure difference according to claim 1, further comprising:

obtaining regional information of a coronary system where a lesion is located according to each spatial model;

correcting the first blood vessel pressure difference $\Delta p_1$ according to the regional information, so as to obtain a corrected third blood vessel pressure difference $\Delta p_3$, wherein the third blood vessel pressure difference $\Delta p_3$ and the first blood vessel pressure difference $\Delta p_1$ satisfy the following relationship:

$$\Delta p_3 = \omega * \Delta p_1, \omega \text{ is a correction parameter, and } 0.5 \leq \omega \leq 1.$$

4. The method for obtaining a blood vessel pressure difference according to claim 3, wherein the regional information comprises one or more of the following: a left main artery, a left anterior descending artery, a left circumflex artery, a right coronary artery, and a branch vessel.

5. The method for obtaining a blood vessel pressure difference according to claim 4, wherein the correction parameter ω satisfies one or more of the following:

when the left main artery needs to be processed, the correction parameter ω=1;

when the left anterior descending artery needs to be processed, the correction parameter ω=0.9~1.0;

when the left circumflex artery needs to be processed, the correction parameter ω=0.65~0.85;

when the right coronary artery needs to be processed, the correction parameter ω=0.75~0.9;

when the branch vessel needs to be processed, the correction parameter ω=0.5~0.85.

6. A system for obtaining a blood vessel pressure difference, comprising:

an image device configured to obtain image data in at least one cardiac cycle;

a processor configured to:

select a plurality of feature times in the one cardiac cycle;

generate spatial models of a target region blood vessel corresponding to each of the feature times according to the image data;

establish a first cross-section model of the target region blood vessel at each position along an axial direction of the target region blood vessel according to each of the spatial models;

establish a corresponding first cross-section function according to each first cross-section model;

along the time sequence, the plurality of feature times are sequentially $t_1, t_2, \ldots, t_q$; along the axial direction of the target region blood vessel, the first cross-section functions corresponding to the first cross-section models at each position 1, 2, . . . ,r from a proximal end to a distal end of the target region blood vessel are $d_1$, $d_2$, . . . , dr; and the processor being further configured to:

establish a first cross-section matrix A according to a correspondence relationship between the first cross-section function and the feature time and position, $$A = \begin{bmatrix} A_{11} & A_{12} & \ldots & A_{1q} \\ A_{21} & A_{22} & \ldots & A_{2q} \\ \vdots & \vdots & \vdots & \vdots \\ A_{r1} & A_{r2} & \ldots & A_{rq} \end{bmatrix}$$

wherein, $A_{rq}$ is the first cross-section function dr corresponding to the first cross-section model at the feature time $t_q$, at the position r of the target region blood vessel; q=r or q≠r, and q and r are positive integers;

wherein the first cross-section model comprises a second cross-section model at different scales, and the processor being further configured to:

establish a corresponding second cross-section function according to the second cross-section model at each scale; and establish a second cross-section matrix at different scales according to a correspondence relationship between the second cross-section function and the feature time and position, wherein, the scale is the distance between two adjacent positions;

wherein the scale includes a first scale, a second scale, ..., an $n^{th}$ scale, and the processor being further configured to:

establish, according to the second cross-section matrix at each scale, a second difference function between the second cross-section functions corresponding to two adjacent positions of the target region blood vessel at different scales in a column direction; and establish, according to the second difference function at the first scale, the second scale, ..., the $n^{th}$ scale, a second variation function $f1x, f2x, \ldots, fnx$ of the corresponding target region blood vessel that is changed with a distance x from any position to a reference point, wherein, n is a positive integer greater than 1;

and the processor being further configured to:

obtain a blood flow model of the target region blood vessel according to the image data;

obtain a blood flow velocity V of the target region blood vessel according to the blood flow model;

obtain a first blood vessel pressure difference $\Delta p1$ at each feature time according to the blood flow velocity V and the second variation functions $f1x, f2x, \ldots, fnx$; and weight and sum the first blood vessel pressure difference $\Delta p_1$ according to a ratio of a time interval between each feature time and the adjacent feature time in one cardiac cycle so as to obtain a second blood vessel difference $\Delta p_2$.

7. The system for obtaining a blood vessel pressure difference according to claim 6, wherein a calculation formula of the first blood vessel pressure difference $\Delta p_1$ at different scales is:

$$\Delta p_1 = (c_1 V + c_2 V^2 + \ldots + c_m V^m) * [\alpha_1 * \int f_1(x) dx + \alpha_2 * \int f_2(x) dx + \ldots + \alpha_n * \int f_n(x) dx], \text{ wherein,}$$

$c_1, c_2, \ldots, c_m$ are reference coefficients of blood flow velocity V, respectively;

$\alpha_1, \alpha_2, \ldots, \alpha_n$ are weighting coefficients of the second variation function $f_1(x), f_2(x), \ldots, f_n(x)$ at different scales, respectively;

m, n are positive integers.

8. The system for obtaining a blood vessel pressure difference according to claim 6, wherein the device further comprising:

a regional information obtaining module configured to obtain, according to each spatial model, regional information of a coronary artery system where a lesion is located; a third blood vessel pressure difference obtaining module configured to correct the first blood vessel pressure difference $\Delta p_1$ according to the regional information, so as to obtain a corrected third blood vessel pressure difference $\Delta p_3$, wherein, the third blood vessel pressure difference $\Delta p_3$ and the first blood vessel pressure difference $\Delta p_1$ satisfy the following relationship:

$\Delta p_3 = \omega * \Delta p_1, \omega$ is a correction parameter, $0.5 \leq \omega \leq 1$.

9. The system for obtaining the blood vessel pressure difference according to claim 8, wherein the regional information includes one or more of the following: a left main artery, a left anterior descending artery, a left circumflex artery, a right coronary artery, and a branch vessel.

10. The system for obtaining a blood vessel pressure difference according to claim 9, wherein the correction parameter $\omega$ satisfies one or more of the following:

when the left main artery needs to be processed, the correction parameter $\omega=1$;

when the left anterior descending artery needs to be processed, the correction parameter $\omega=0.9\sim1.0$;

when the left circumflex artery needs to be processed, the correction parameter $\omega=0.65\sim0.85$;

when the right coronary artery needs to be processed, the correction parameter $\omega=0.75\sim0.9$;

when the branch vessel needs to be processed, the correction parameter $\omega=0.5\sim0.85$.

\* \* \* \* \*